(12) United States Patent
Martel et al.

(10) Patent No.: US 11,884,547 B2
(45) Date of Patent: Jan. 30, 2024

(54) CHALCOGEN-GRAFTED CARBON MATERIALS AND PROCESSES FOR THEIR PREPARATION

(71) Applicant: Valorisation-Recherche, Montreal (CA)

(72) Inventors: Richard Martel, Montreal (CA); Rafaella Oliveira Do Nascimento, Kitchener (CA); Pierre Lévesque, Kitchener (CA)

(73) Assignee: Valorisation-Recherche, Limited Partnership, Montreal (CA)

( * ) Notice: Subject to any disclaimer, the term of this patent is extended or adjusted under 35 U.S.C. 154(b) by 126 days.

(21) Appl. No.: 17/270,298

(22) PCT Filed: Aug. 23, 2019

(86) PCT No.: PCT/CA2019/051161
§ 371 (c)(1),
(2) Date: Feb. 22, 2021

(87) PCT Pub. No.: WO2020/037428
PCT Pub. Date: Feb. 27, 2020

(65) Prior Publication Data
US 2021/0179433 A1    Jun. 17, 2021

Related U.S. Application Data

(60) Provisional application No. 62/722,524, filed on Aug. 24, 2018.

(51) Int. Cl.
*C01B 32/194* (2017.01)
*B82Y 30/00* (2011.01)
*B82Y 40/00* (2011.01)

(52) U.S. Cl.
CPC .............. *C01B 32/194* (2017.08); *B82Y 30/00* (2013.01); *B82Y 40/00* (2013.01); *C01P 2002/82* (2013.01)

(58) Field of Classification Search
CPC ... C01B 32/194; C01B 32/00; C01B 2202/02; C01B 32/156; C01B 32/168;
(Continued)

(56) References Cited

U.S. PATENT DOCUMENTS 9,005,808 B2    4/2015    Abouimrane et al.
9,896,340 B2    2/2018    Tour et al.
(Continued)

OTHER PUBLICATIONS

White, et al., Formation of Polycyclic Thiophenes from Reaction of Selected Polycyclic Aromatic Hydrocarbons with Elemental Sulfur and/or Pyrite under Mild Conditions, Energy & Fuels 1988; 2: 220-223 (Year: 1988).*
Luong, et al., Functional Graphene by Thiol-ene Click Chemistry, Chem. Eur. J. 2015; 21: 3183-3186 (Year: 2015).*
Chuang, et al., Fine tuning the orifice size of an open-cage fullerene by placing selenium in the rim: insertion/release of molecular hydrogen, Chem. Commun. 2007: 1278-1280 (Year: 2007).*
(Continued)

*Primary Examiner* — Daniel C. McCracken
(74) *Attorney, Agent, or Firm* — Hovey Williams LLP; Crissa A. Cook

(57) ABSTRACT

Chalcogen-grafted carbon material as well as their functionalized forms are described along with processes for their preparation. More specifically, the chalcogen is covalently linked to the carbon scaffold of a polyaromatic carbon via C=X and/or C—X—C bonds. Processes for their preparation include a single thermal treatment without the use of strong acids or anhydrous solvents.

30 Claims, 13 Drawing Sheets

(58) Field of Classification Search
CPC ......... C01B 32/21; B82Y 30/00; B82Y 40/00; C01P 2002/82; C01P 2004/04; H01M 4/0471; H01M 4/13; H01M 4/625; H01M 4/139; H01M 4/38; H01M 4/9075; H01M 4/925; H01M 10/052; H01L 45/141; Y02E 60/10; Y02E 60/13; Y02E 60/50; A61K 8/23; A61Q 5/065; B33Y 70/00
See application file for complete search history.

(56) References Cited

U.S. PATENT DOCUMENTS

| | | | |
|---|---|---|---|
| 2008/0206124 A1* | 8/2008 | Jang | C01B 32/225 423/608 |
| 2016/0054253 A1 | 2/2016 | Zhou et al. | |
| 2016/0240841 A1 | 8/2016 | He et al. | |
| 2016/0336590 A1 | 11/2016 | Manthiram et al. | |
| 2017/0229703 A1 | 8/2017 | Chu et al. | |

OTHER PUBLICATIONS

Xia, et al., Selenium-Functionalized Graphene Oxide That Can Modulate the Balance of Reactive Oxygen Species, ACS Appl. Mater. Interfaces 2017; 9: 21413-21421 (Year: 2017).*

Plachinda, et al., Electrical Properties of Covalently Functionalized Graphene, Aims Materials Science 2017; 4(2): 340-362 (Year: 2017).*

International Search Report and Written Opinion in corresponding PCT/CA2019/051161, dated Oct. 25, 2019.

White, et al., "Formation of polycyclic thiophenes from reaction of selected polycyclic aromatic hydrocarbons with elemental sulfur and/or pyrite under mild conditions", Energy Fuels 1988, 2 (2), 220-223.

Nakamura, et al., "Chemical modification of single-walled carbon nanotubes with sulfur-containing functionalities", Diamond and Related Materials, 16 (4-7), Apr.-Jul. 2007, 1091-1094.

Curran, et al., "Thiolation of carbon nanotubes and sidewall functionalization", J. Mater. Res., 21 (4), Apr. 2006, 1012-1018.

* cited by examiner

Figure 3(a) – (d)
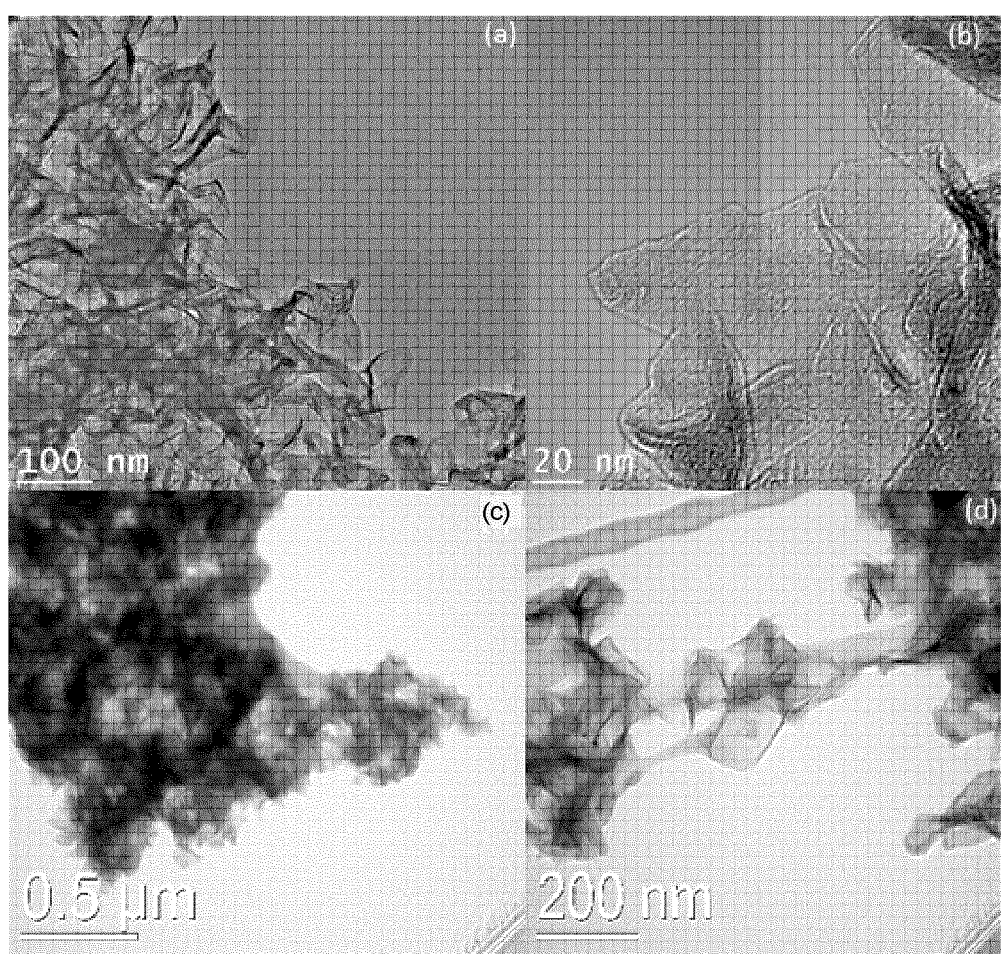

Figure 3(e) – (z)
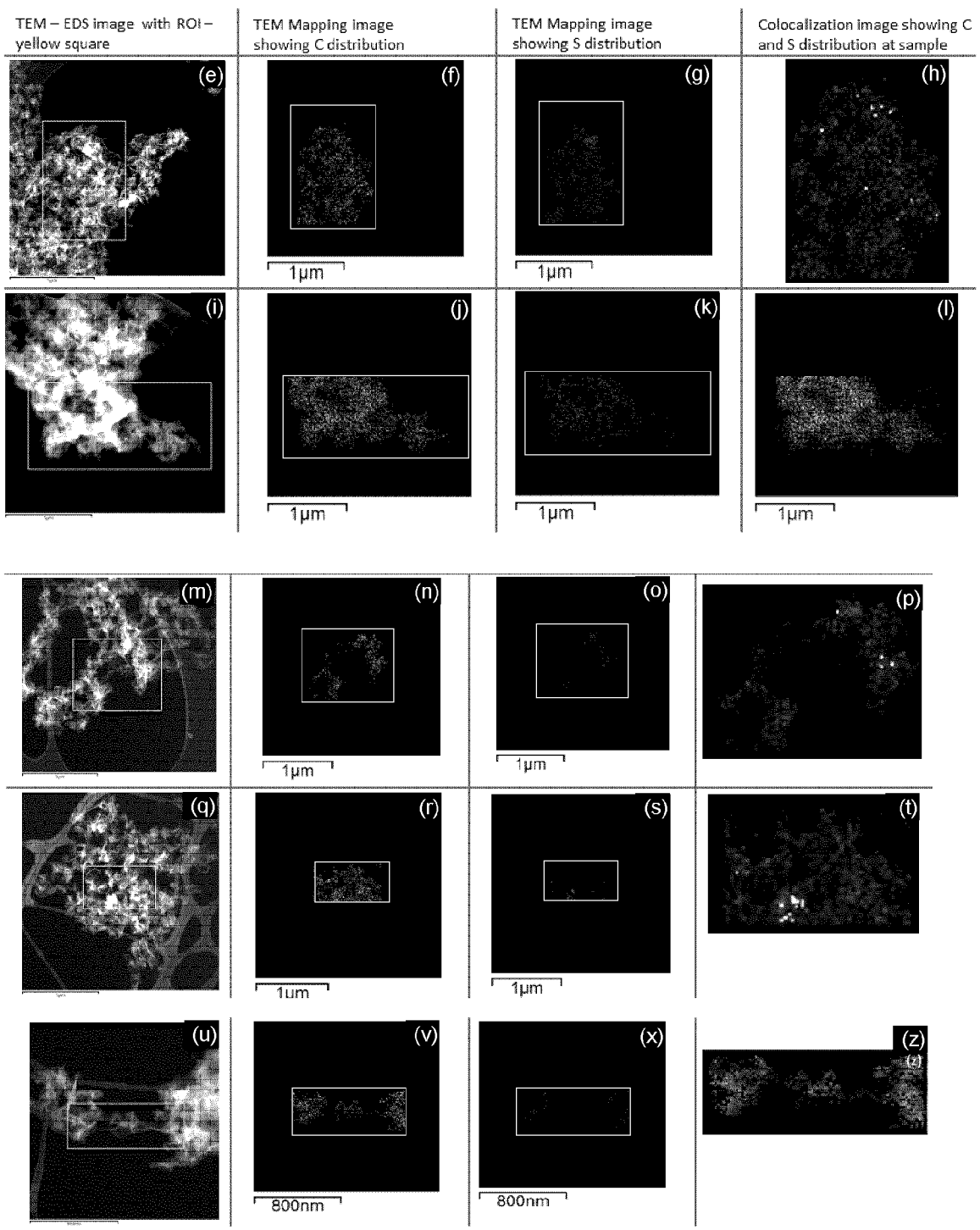

Figure 7
(a)
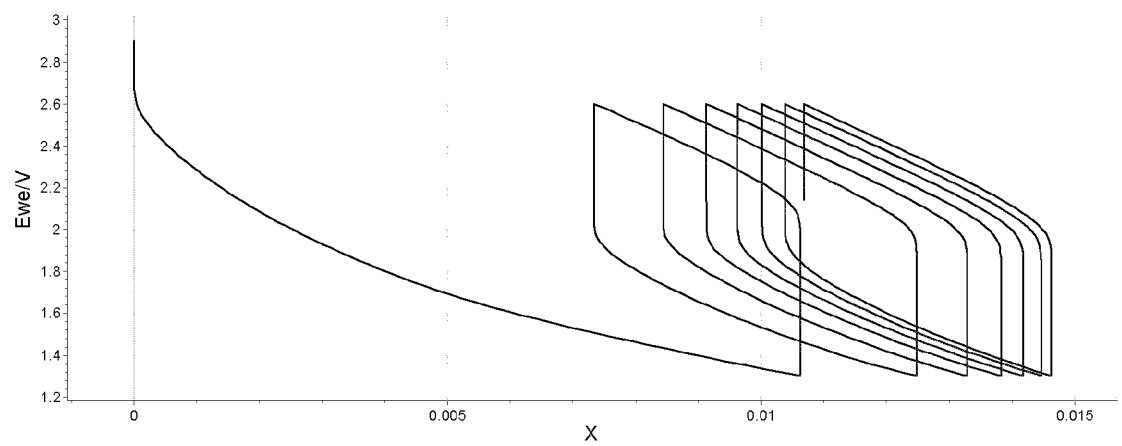
(b)
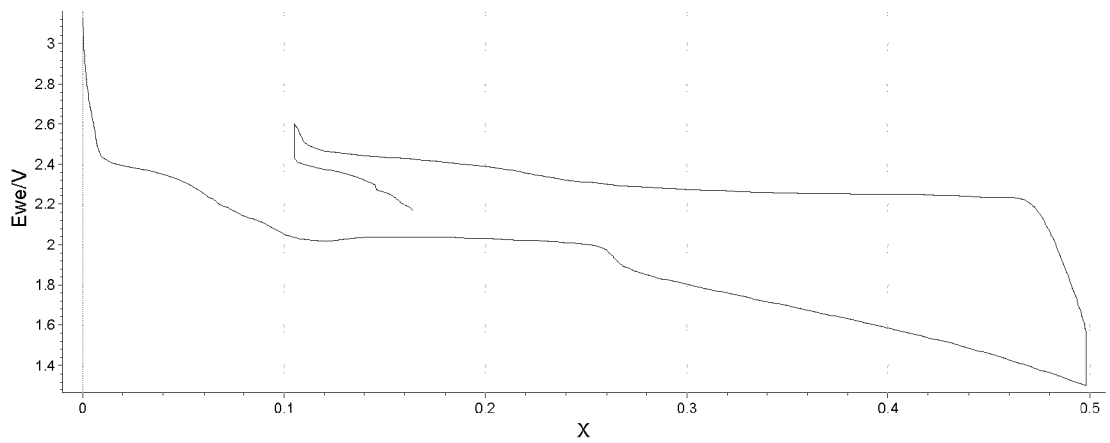

Figure 9
② live and dead assay    day5
(a)
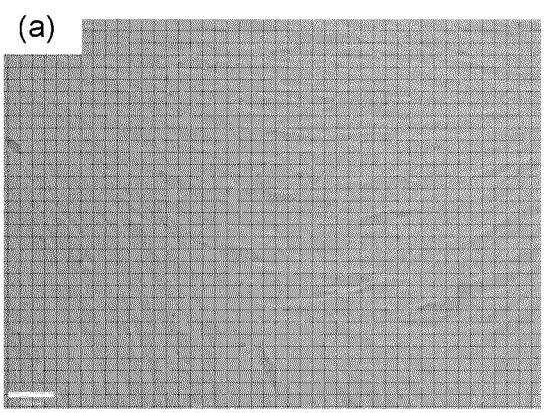
normal cell
(b)
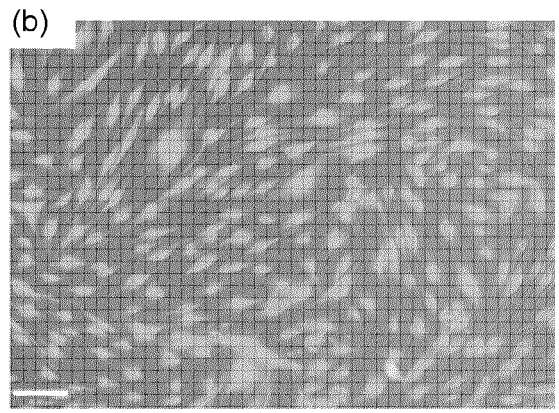
cell(control)
(c)
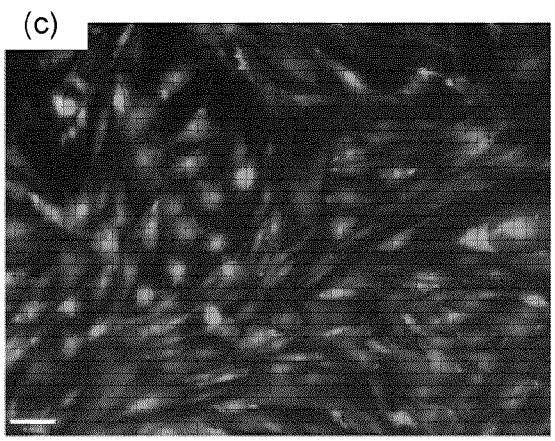
Graphene
(d)
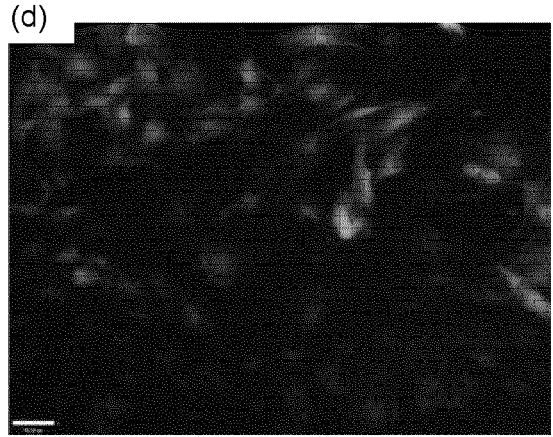
Graphene + Sulfur

CHALCOGEN-GRAFTED CARBON MATERIALS AND PROCESSES FOR THEIR PREPARATION

RELATED APPLICATIONS

This application is the U.S. National Stage of International Patent Application No. PCT/CA2019/051161, filed Aug. 23, 2019, which claims priority under applicable law to U.S. provisional application No. 62/722,524 filed on Aug. 24, 2018, the content of each being incorporated herein by reference in its entirety for all purposes.

TECHNICAL FIELD

The technical field generally relates to modified carbons, such as graphene, especially chalcogen-modified carbons, processes for their preparation and uses thereof.

BACKGROUND

Graphene is a material with unique physical, mechanical and electrical properties, which are studied in a wide spectrum of applications, for biomedical devices as well as in semiconductors, solar cells, batteries, supercapacitors, biosensors, ions and pressure sensors, MEMs, etc.

Graphene is generally functionalized before it can be used. The first step in the functionalization of graphene generally involves the production of graphene oxide (GO) or reduced graphene oxide (RGO). However, processes used for GO and RGO productions involve multiple pre- and post-treatment steps, generating a great variability in the resulting products even when using the same procedure. Graphene oxide production processes also generally involve harsh conditions such as strong acids, radical oxygen, etc. These reactions modify the material irreversibly with surface functions such as hydroxyl, epoxide, etc. Currently available methods are costly, time-consuming, and generate substantial amounts of chemical wastes.

SUMMARY

One aspect of the present technology relates to chalcogen-grafted carbon, where the carbon is a polyaromatic carbon and the chalcogen X is covalently linked to the carbon via C=X and/or C—X—C bonds.

In one embodiment, the carbon is selected from graphene, graphite, carbon foams, and nanocarbons, which include but not limited to nanohorns, fullerenes (e.g. $C_{60}$) and carbon nanotubes. For instance, the carbon is graphene.

In another embodiment, X is a chalcogen selected from S, Se and Te. For example, X is S. In another embodiment, wherein the molar ratio of carbon:chalcogen (C:X) is within the range of from 2:1 to 1:1000, or within the range of from 3:1 to 100:1, or within the range of from 3:1 to 10:1. In a further embodiment, the chalcogen is sulfur and the weight concentration of chalcogen in the chalcogen-grafted carbon is from 1 wt % to 50 wt %, or from 3 wt % to 47 wt %.

In one embodiment, the polyaromatic carbon comprises 5-membered, 6-membered and 7-membered rings in a fused rings system. In a further embodiment, the polyaromatic carbon comprises mainly 6-membered rings in a fused rings system.

In yet another embodiment, the chalcogen-grafted carbon comprises units of the formula:

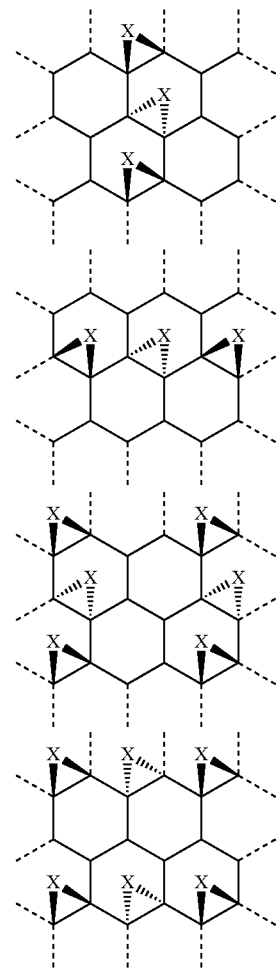

wherein X is as herein defined.

In one embodiment, the chalcogen-grafted carbon further comprises C=X bonds.

Another aspect of the present technology relates to functionalized chalcogen-grafted carbon, wherein the carbon is a polyaromatic carbon comprising C—X—C and C=X bonds, and is functionalized with —XH, —XR, or a combination thereof, or a complex or salt thereof, wherein X is a chalcogen covalently linked to the carbon, and R is a functional group, or an X of a second functionalized chalcogen-grafted carbon thereby linked by a dichalcogenide bond, wherein the chalcogen-grafted carbon is as herein defined.

In one embodiment, the polyaromatic carbon is functionalized with —XH or a salt or a metal complex thereof. In another embodiment, the C—X—C, C=X, —XH and/or —XR form a complex with a metal ion or a metal aggregate (e.g. metallic nanoparticles made of a transition metal, such as Pt, Ni, Co, Cu, Ru, Au and Ag, or a transition metal alloy). In a further embodiment, the polyaromatic carbon is functionalized with —XR, where R is an antibody tag (e.g. a group like SATA, SMCC, and SPDP), an alkyl, allyl, benzyl, phenyl, a polymer, MAL-PEG-NHS, SMCC-PEG-NHS, MAL-PEG-BIOTIN, SMCC-PEG-Biotin, or any other biocompatible polymers.

A further aspect of the present technology relates to a process for the preparation of a chalcogen-grafted carbon as herein defined, comprising the steps of:

(a) disposing a polyaromatic carbon in a first compartment and a chalcogen in a second compartment, where the first and second compartments are connected to allow gaseous exchange without direct physical contact between the polyaromatic carbon and chalcogen; and
(b) simultaneously heating the first compartment at a first temperature and the second compartment at a second temperature;

wherein the first temperature is higher than the second temperature and wherein the second temperature allows the sublimation of the chalcogen.

In one embodiment, the first and second compartments are part of a dumbbell-shape ampoule. In another embodiment, the first and second compartments are reactors.

In another embodiment, the second temperature is within the range of from 100° C. to 950° C. In another embodiment, the chalcogen X is S and the second temperature is within the range of from 100° C. to 650° C., or from 200° C. to 500° C., or from 150° C. to 650° C., or from 150° C. to 450° C. In another embodiment, the chalcogen X is Se and the second temperature is within the range of from 220° C. to 800° C., or from 180° C. to 650° C., or from 230° C. to 700° C., or from 200° C. to 600° C., or from 190° C. to 500° C. In a further embodiment, the chalcogen X is Te and the second temperature is within the range of from 350° C. to 950° C., or from 300° C. to 850° C., or from 550° C. to 750° C., or from 400° C. to 700° C., or from 550° C. to 950° C., or from 500° C. to 650° C., or from 330° C. to 550° C.

In yet a further embodiment, the first temperature is a temperature which is 500° C. or less, higher than the second temperature, or between 10° C. and 200° C. higher than the second temperature.

An additional aspect of the present technology relates to a process for producing a functionalized chalcogen-grafted carbon, comprising the step of reacting a chalcogen-grafted carbon as defined herein with a nucleophile, an oxidant such as $HNO_3$ or $O_2$, a reducing agent such as $LiAlH_4$, a metal or a metallic salt or complex.

BRIEF DESCRIPTION OF THE DRAWINGS

FIG. 3 shows (a)-(d) TEM images of sulfur-grafted graphene samples. Other TEM images of the sulfur-grafted graphene samples are shown in (e)-(z). The regions of interest (ROI) indicated by squares are investigated further using EDS mode to obtain the carbon distribution (f, j, n, r, v) and of the sulfur distribution (g, k, o, s, x) of each sample. Images in (h),(l),(p),(t) show the colocalization of the carbon and sulfur distributions obtained in EDS mode, as detailed in Example 1.

FIG. 7 shows (a) graphene and (b) GS results of preliminary galvanostatic cycling tests for the application of the materials as electrodes of batteries.

FIG. 9 shows images of a cell viability of initial cytotoxicity test (live/Dead™) test: (a) normal cells, (b) control cells, (c) graphene treated cells, and (d) graphene-sulfur (GS) treated cells.

DETAILED DESCRIPTION

Figure 1:
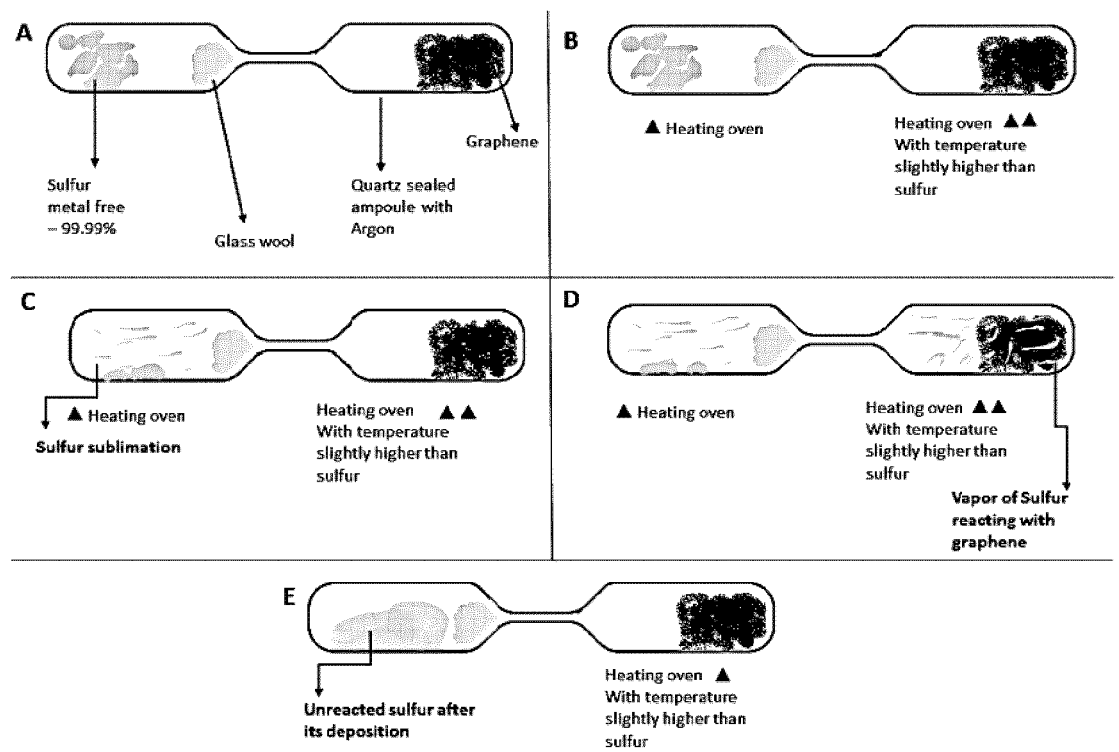
FIG. 1 illustrates schematically the process according to one embodiment, including (A) a dumbbell-shaped quartz ampoule having sulfur and graphene in each compartment and a bridge or a narrow constriction, including glass wool (optional) allowing gas exchange while preventing direct physical contact between the two solids; (B) each side being heated, the temperature on the graphene side being slightly higher; (C) sulfur subliming on the left side; (D) sublimed sulfur travelling in gaseous form to the graphene side of the ampoule to react therewith; and (E) after the reaction is complete, unreacted sulfur remains on the left side while the right side contains grafted graphene.

The following detailed description and examples are illustrative and should not be interpreted as further limiting the scope of the invention.

All technical and scientific terms and expressions used herein have the same definitions as those commonly understood by the person skilled in the art when relating to the present technology. The definition of some terms and expressions used herein is nevertheless provided below for clarity purposes.

The term "polyaromatic carbon" as used herein refers to delocalized conjugated π systems including a number of u delocalized electrons that is equal to $(4n+2)\pi$ electrons in a fused rings system, where n is an integer. The polyaroatic carbon may comprise 6-membered rings in the system and may further comprise other ring sizes such as 5-membered linked to 7-membered rings (i.e. pentagon-heptagon pairs) and any other combinations of rings with preserved aromaticity. It is understood that, when the polyaromatic carbon as defined herein is chalcogen-grafted, then the delocalization may be at least in part disrupted by the grafted chalcogen atoms.

The term "chalcogen" as used herein, also represented by "X", includes a compound of group 16 of the periodic table of elements but excludes oxygen.

When the term "approximately" or its equivalent term "about" are used herein, it means in the region of, and around. When the terms "approximately" or "about" are used in relation to a numerical value, it modifies such numerical value. For example, the use of this term could mean above and below its nominal value by a variation of 10%. This term may also take into account the probability of random errors in experimental measurements or rounding.

The present description generally relates to a process for preparing a chalcogen-grafted carbon material having C=X or C—X—C bond as well as the material thus obtained and its applications, for example, in the preparation of functionalized carbon via nucleophilic displacements, salt formation or metal interactions. The chalcogen-grafted carbon may also include or be further modified to include dichalcogenide (X—X) bonds.

The present process comprises a sublimation setup of chalcogens across a temperature gradient, which provides the conditions required to obtain interaction between chalcogen atoms in the gas phase and the carbon nanostructures in the solid phase. With this set up, there is no need to add steps involving the mixing of reaction precursors or sample purification after reaction.

The process for the preparation of a chalcogen-grafted carbon as herein defined mainly comprises the steps of:
  (a) disposing a polyaromatic carbon in a first compartment and a chalcogen in a second compartment, where the carbon and chalcogen are not in direct physical contact, the first and second compartments being connected in a manner allowing gaseous exchange; and
  (b) simultaneously heating the first compartment at a first temperature and the second compartment at a second temperature;

where the first temperature is higher than (or equal to) the second temperature and wherein the second temperature allows the sublimation of the chalcogen. Preferably, the first temperature is higher than the second temperature.

For example, the first and second compartments are part of a dumbbell-shape ampoule, such as a dumbbell like quartz ampoule filled with argon (Ar) and sealed on both sides. In this case, each side of the dumbbell forms one of the two compartments. The first compartment of the ampoule contains graphene and the second section contains a chalcogen (e.g. S, Se or Te).

FIG. 1 illustrates a scheme of reaction using such a two-sided ampoule, where in this case, glass wool is placed at the bridge in between to avoid physical mixing of the reagents. FIG. 1(a) shows the quartz ampoule having high purity sulfur (99.99% purity and metal free) on the left side of the ampoule and graphene on the right side of the ampoule. FIG. 1(b) shows the reaction set up where the temperature on the graphene side is slightly higher than the temperature on the other side of the ampoule. This avoids the deposition of unreacted sulfur on the graphene side.

As the reaction starts, (c) shows the sublimation of the sulfur with increasing temperature. In FIG. 1(d), the sublimed sulfur travels to the other compartment of the ampoule to react with graphene. FIG. 1(e) illustrates the accumulation of unreacted sulfur on the left side of the ampoule with no further contamination of the graphene after its reaction. The remaining unreacted sulfur can thus be recovered and re-sublimed to react further with more graphene.

It is understood that the process illustrated in FIG. 1 could be scaled up using equivalent apparatus or be adapted to manufacturing capabilities such that the first and second compartments would each be a reactor as long as the starting material are preferably not in direct physical contact, but the two reactors are connected in a manner allowing gaseous exchanges. Furthermore, the process can be adapted to work in one- or two-sided ampoules without temperature gradient. The process requires, however, an evaluation of the amount of reactant and may require separation of unreacted reactants from products using, for instance, extraction by a solvent or a sublimation of the unreacted chalcogen.

The temperatures in each compartment are selected based on the materials being reacted, for example the second temperature (the chalcogen temperature) can be within the range of from 100° C. to 950° C. For instance, the chalcogen is sulfur and the second temperature is within the range of from 100° C. to 650° C., or from 200° C. to 500° C., or from 150° C. to 650° C., or from 150° C. to 450° C. In another example, the chalcogen is selenium and the second temperature is within the range of from 220° C. to 800° C., or from 180° C. to 650° C., or from 230° C. to 700° C., or from 200° C. to 600° C., or from 190° C. to 500° C. When the chalcogen is tellurium, the second temperature may be within the range of from 350° C. to 950° C., or from 300° C. to 850° C., or from 550° C. to 750° C., or from 400° C. to 700° C., or from 550° C. to 950° C., or from 500° C. to 650° C., or from 330° C. to 550° C.

For a two-sided ampoule, the first temperature (the carbon temperature) is preferably higher than the chalcogen temperature, for instance, at least 10° C. higher than the chalcogen temperature, at least 80° C. higher than the chalcogen temperature, at a temperature which is between 1° C. and 650° C., between 1° C. and 500° C., or between 10° C. and 200° C. higher than the chalcogen temperature. For instance, the first temperature is within the range of from 180° C. to 300° C. for sulfur, or from 200° C. to 550° C. for selenium or from 20° C. to 700° C. for tellurium, higher than the second temperature. In other examples, the difference between the first and second temperature is zero or in the range between −1 and −300° C.

For the one-sided ampoule or two-sided ampoule without temperature gradient, the temperature is selected based on the materials being reacted, for example from 100° C. to 950° C. For instance, the chalcogen is sulfur and the temperature is within the range of from 100° C. to 650° C., or from 200° C. to 500° C., or from 150° C. to 650° C., or from 150° C. to 450° C. In another example, the chalcogen is selenium and the temperature is within the range of from 220° C. to 800° C., or from 180° C. to 650° C., or from 230° C. to 700° C., or from 200° C. to 600° C., or from 190° C. to 500° C. When the chalcogen is tellurium, the temperature may be within the range of from 350° C. to 950° C., or from 300° C. to 850° C., or from 550° C. to 750° C., or from 400° C. to 700° C., or from 550° C. to 950° C., or from 500° C. to 650° C., or from 330° C. to 550° C.

The material thus prepared is not merely a carbon/chalcogen mixture but rather a chalcogen-grafted carbon as shown in TEM images in EDS mode and Raman spectra, and further discussed in the Examples section. The carbon used as starting material for grafting is generally a $sp^2$ carbon source, i.e. having a polyaromatic structure, such as graphene and other nanocarbons. The chalcogen X reacts with the carbon structure to produce covalently linked chalcogen atoms without hydrogen atoms (i.e. S linked to carbon rather than SH). The chalcogen is thus linked to the carbon structure via C=X and/or C—X—C bonds.

An example of C—X—C bonds within the carbon backbone is illustrated by any one of the following:

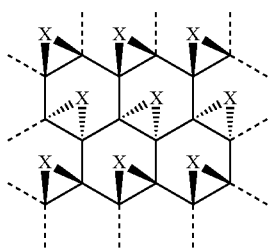
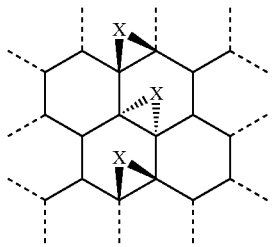
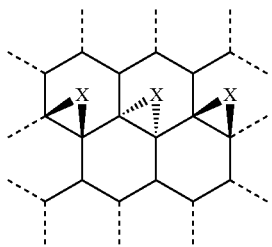
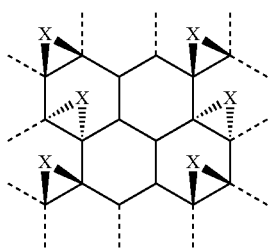
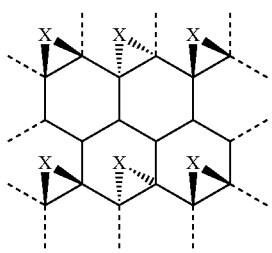

The carbon sp² structure thus becomes near-sp³ hybridized in these reacted parts of the carbon structure. C=X bonds will be located at the periphery of a polyaromatic structure, i.e. on the outside rings with respect to the polyaromatic structure. The chalcogen X is selected from S, Se and Te.

For example, the structure of a grafted part of a carbon structure may be illustrated as follows:

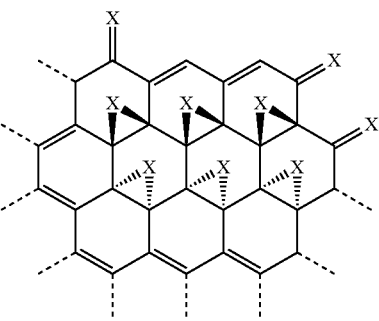

The carbon used as starting material is a lattice of sp²-hybridized polyaromatic carbon, for instance, graphene, graphite, carbon foams, and nanocarbons, including but not limited to nanohorns, fullerenes and/or carbon nanotubes. In one example, the carbon structure is graphene. In another example, the polyaromatic carbon is a single-wall carbon nanotube (SWCNT).

The chalcogen-grafted carbon as herein defined, for instance, may follow the following formula:

$$C_{2n}S_2$$

wherein n≥2.

For instance, n is within the range of from 2 to 200, or from 2 to 100, or from 3 to 50, or from 3 to 10, or from 3 to 6, or from 4 to 10, or from 5 to 10, or from 6 to 20. For example, the molar ratio of carbon:chalcogen is within the range of from 2:1 to 1000:1, or from 2:1 to 100:1, or from 3:1 to 100:1, or from 3:1 to 20:1, or from 3:1 to 10:1, or from 3:1 to 6:1, or from 4:1 to 10:1, or from 5:1 to 10:1, or from 6:1 to 20:1. For example, the content of grafted chalcogen in the chalcogen-grafted carbon as herein defined where the chalcogen is sulfur may be 1 wt % to 50 wt %, or 3 wt % to 50 wt %, or 3 wt % to 47 wt %, or from 10 wt % to 50 wt %.

The present description also relates to a process for producing a functionalized chalcogen-grafted carbon, comprising the step of reacting a chalcogen-grafted carbon as herein defined with a nucleophile, an oxidant such as $HNO_3$ or $O_2$, a reducing agent such as $LiAlH_4$, a metal or a metallic salt or complex.

Figure 5:
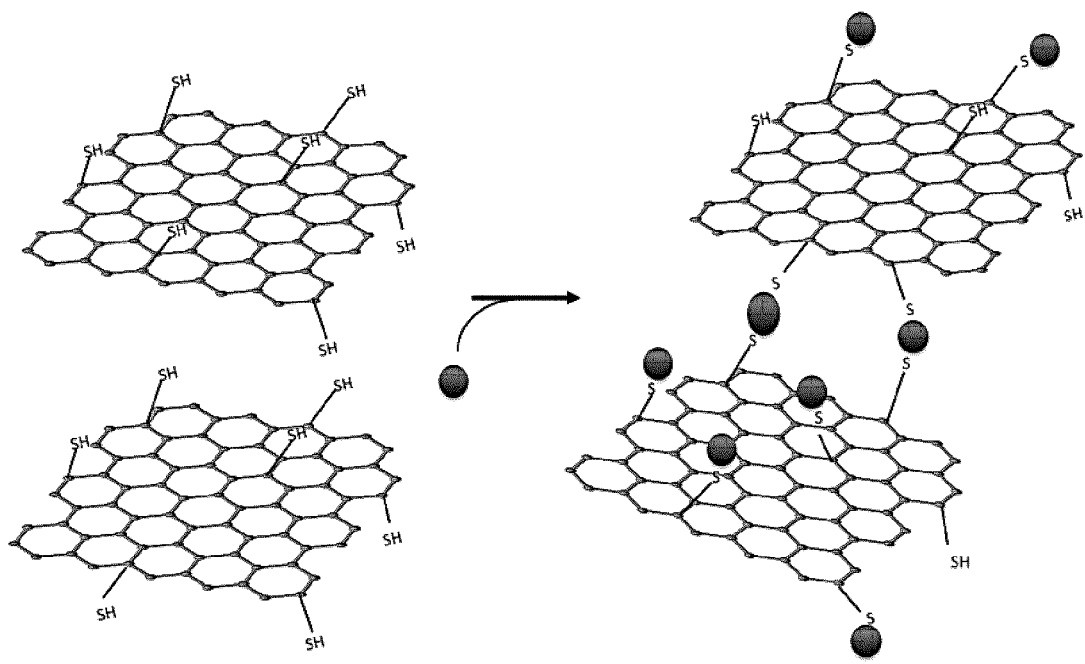
FIG. 5 is a schematic representation of one embodiment of a sulfur-grafted graphene further functionalized with the opening of C—S—C rings to generate thiol (—SH) groups, here coordinated with metal nanoparticles, for instance, creating an aggregation with A-B stacking.

This additional step or series of steps results in the opening of the 3-membered rings and the generation of X—, XH, or XR groups which may be further functionalized or coordinated to a metal, a metal ion or a metal aggregate including metallic nanoparticles (e.g. metallic nanoparticles made of a transition metal, such as Au, Ag, Ni, Co, Cu, Ru or Pt). The latter are illustrated in FIG. 5, where the small spheres represent metal nanoparticles interacting with XH groups after modification.

Figure 6:
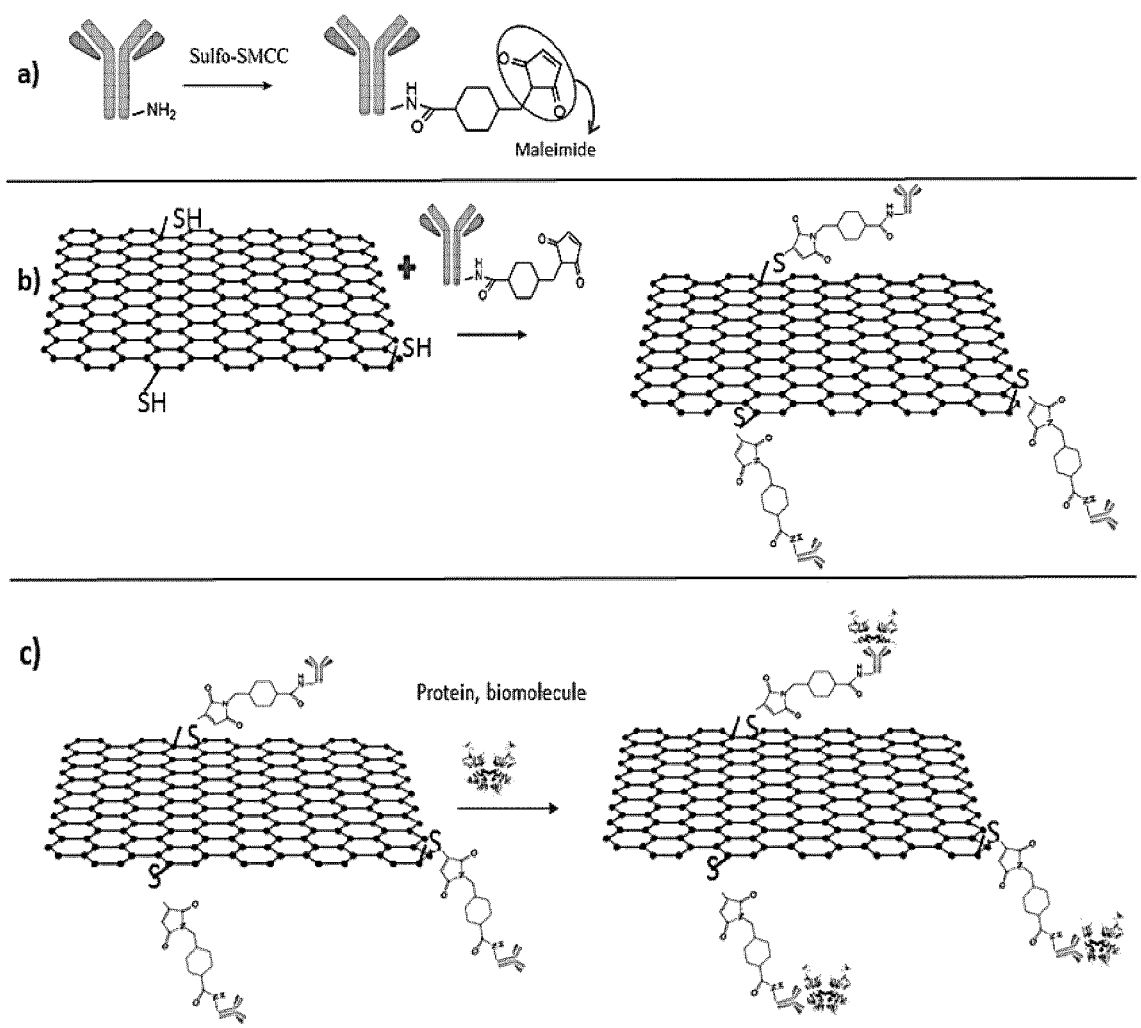
FIG. 6 is a schematic representation of an embodiment of a process for functionalizing a sulfur-grafted graphene by (a) maleimide tagging of IgG antibodies by cross-linking with sulfo-SMCC; (b) maleimide-antibody attachment on thiol groups of a graphene-chalcogenide; and (c) application of functionalized graphene-chalcogenide as a platform to the live attachment of proteins, biomolecules or cells aiming for further quantification.

Another example of a functionalized chalcogen-grafted carbon is illustrated in FIG. 6, where (a) an antibody is first tagged with a maleimide by cross-linking with sulfo-SMCC or a commercially available tagged antibody is used; (b) the tagged antibody is attached to thiol groups on the carbon surface; and (c) the functionalized carbon is further used as a platform for the attachment, for instance, of proteins, biomolecules or living cells. A further example includes the use of antibody coated metallic nanoparticles for interaction with the thiol groups on the modified graphene surface.

The above modified carbon may thus be called a functionalized chalcogen-grafted carbon, where the carbon is a polyaromatic carbon comprising C—X—C and C=X bonds, and is further functionalized with —XH, —XR, or a combination thereof, or a coordinated complex or salt thereof, wherein X is as defined herein and is covalently linked to the carbon, and R is a functional group. R may also be the chalcogen X of a second functionalized chalcogen-grafted carbon thereby linked by a dichalcogenide bond. As the functionalized chalcogen-grafted carbon is derived from the chalcogen-grafted carbon defined above, the variations, concentrations, ratios, defined for the latter will also apply to the former.

Additionally, the group —XH may further form a salt or a metal complex. For example, —XH forms a complex with a metal. For instance, the polyaromatic carbon comprises C—X—C and C=X bonds, and is further functionalized with —XH, —XR, or a combination thereof, wherein the C—X—C, C=X, —XH and/or —XR form a complex with a metal ion or metal aggregate (e.g. metallic surfaces or nanoparticles made of a transition metal, such as Pt, Ni, Co, Cu, Ru, Au and Ag, or an alloy of a transition metal).

Also, when the carbon is functionalized with a —XR group, the R may be an antibody tag (e.g. a group like succinimidyl acetylthioacetate (SATA), succinimidyl trans-4-(maleimidylmethyl)cyclohexane-1-carboxylate (SMCC) and succinimidyl 3-(2-pyridyldithio)-propionate (SPDP)), an alkyl, allyl, benzyl or phenyl group, a polymer (e.g. PET) or a biopolymer (e.g. MAL-PEG-NHS, SMCC-PEG-NHS, MAL-PEG-BIOTIN, SMCC-PEG-Biotin, etc.).

The chalcogen-grafted carbon or its functionalized version may thus be used in several fields from rechargeable batteries, fuel cells, supercapacitors, additive manufacturing (or 3D printing), dark coatings, dying fabrics and human hair, and biomedical applications, such as the development of kits to cellular, pollutant removal, or biomolecular identification, as well as applications in cell scaffolding to growth/differentiation.

Regarding their use in batteries, as the sulfur atoms are covalently linked to the carbon structure, their use in electrodes could reduce or prevent the formation of soluble lithium sulfide entities such as $Li_2S$, thereby reducing the so-called shuttle effect in lithium/sulfur and lithium-ion batteries and improve capacity retention, or help achieve better mechanical properties of the electrodes, using for instance a mixture with polymer (e.g. PVP) and carbon nanotubes, and prevent degradation, e.g. cracking, delamination, etc.

The chalcogen-grafted carbon or its functionalized version may also be used in the preparation of active electrodes in fuel cells. For instance, the chalcogen-grafted carbon or its functionalized version could replace, completely or in part, the use of other carbon materials as support of the catalyst particles. In such application, the functionalization or coordination of the metal catalyst (e.g. Pt) to the chalcogen-grafted carbon can be used to anchor the metal catalyst, stabilized the nanoparticles after sintering, or stabilized mechanically the electrodes using for example dichalcogenide bonds.

The chalcogen-grafted carbon or its functionalized version may also be used in the preparation of inks for use in printable electronics and 3D printing. For instance, the chalcogen-grafted carbon or its functionalized version could replace, completely or in part, the use of polymers. In such applications, modified graphene or nanotubes could be further modified to form dichalcogenide bonds (X—X) between sheets of polymer, graphene, nanotubes or other nanoparticles during or after deposition.

As indicated above, the functionalized version of the chalcogen-grafted carbon may further be used for the attachment of biomolecules. For example, the XH modified material can be directly bonded with the maleimide of antibodies tagged with sulfo-SMCC cross-linkers. Untagged antibodies can also be bonded to the present material through simple cross-linking reactions using for example, SATA, SMCC or SPDP. A platform may thus be developed for protein or cell identification by promoting their combinations with secondary antibodies (see FIG. 6) labelled with fluorescent probes, gold nanoparticles coated with antibodies (AuNPs@Abs), fluorescence or Raman nanoprobes, etc.

The present material could also be further used as additives to the scaffolds used in stem cells culture and/or differentiation, e.g. in tissue regeneration and human mesenchymal stem cells (MSCs) differentiation. The present material could also be used to modulate the cell's behaviour and induce myogenic, angiogenic, neurogenic, osteogenic, cardiomyogenic, or adipogenic responses. The material may thus be mixed with biocompatible polymers or applied as foam or as a medium to improve the properties of the scaffolds. The present materials can also be mixed with biocompatible polymers or 3D printed structures into scaffolds for similar uses.

Other uses of the present materials may also include black coatings related to dark matter or dark colouring, or as protective materials, or as rubber after cross linking, or as reinforcement agent for concrete, as thin films, lubricants, etc. Other uses include light-weight mechanical membranes such as used in headphones and speakers or any carbon coatings made of this light-weight compound. As this material may interact with metallic nanoparticles, it would also be possible to create black-coated textiles or membranes with unique thermal and/or conductive properties. Finally, the material could also be used in water treatment, for instance, applied to water filters for the removal of pollutants (e.g. by affinity with chalcogenides), small particles, or heavy metals by direct adsorption.

EXAMPLES

The following non-limiting examples are illustrative embodiments and should not be construed as further limiting the scope of the present invention. These examples will be better-understood with reference to the accompanying figures.

Example 1: Synthesis and Characterization a) Preparation of Sulfur-Grafted Graphene and Sulfur-Grafted SWCNTs The syntheses are carried out in a dumbbell-like quartz ampoule filled with argon (Ar) and sealed on both sides (see FIG. 1). For the first example, the first section of the ampoule contains graphene flakes airbrushed onto a $Si/SiO_2$ substrate and the second section contains a chalcogenide (i.e. sulfur) in ~0.5 atm of argon. For the second example, the first section of the ampoule contains deposited single-wall carbon nanotubes (SWCNTs) on a $Si/SiO_2$ substrate and the second section contains a chalcogenide (e.g. sulfur) in 0.5 atm of argon. After sealing, the ampoules are heated up in an oven at a given temperature and time, as indicated in Table 1. For those examples, the difference in temperature between the first (graphene or SWCNT sides) and the second (chalcogenide side) temperatures is between 170° C. and 270° C.

TABLE 1

Experimental conditions of nanocarbon-sulfur reaction

| Sample | Graphene (mg) | Sulfur (mg) | Temperature chalcogenide section (° C.) | Temperature sample section (° C.) | Reaction time (hours) |
|---|---|---|---|---|---|
| RN869A | 2 | 500 | 200 | 370 | 24 |
| RN869C | | | | | 1 |
| RN869F | | | | | 4 |
| RN869H | | | | | 8 |
| RN884C | Airbrushed on Au/Si/SiO2 | 500 | 200 | 370 | 8 |
| SWCNTs on Si/SiO2 | N/A | 500 | 200 | 470 | 24 |
| C60 on Si/SiO2 | N/A | 3000 | 200 | 370 | 24 |
| Control 1 [a] | 2 | 0 | 450 | 450 | 24 |
| Control 2 [b] | 0 | 50 | 200 | 450 | 24 |

[a] Graphene airbrushed on Si/SiO2 (sulfur free)
[b] Si/SiO2 (carbon-free)

b) Characterization of Sulfur-Grafted Graphene and Deposited SWCNTs

Figure 2:
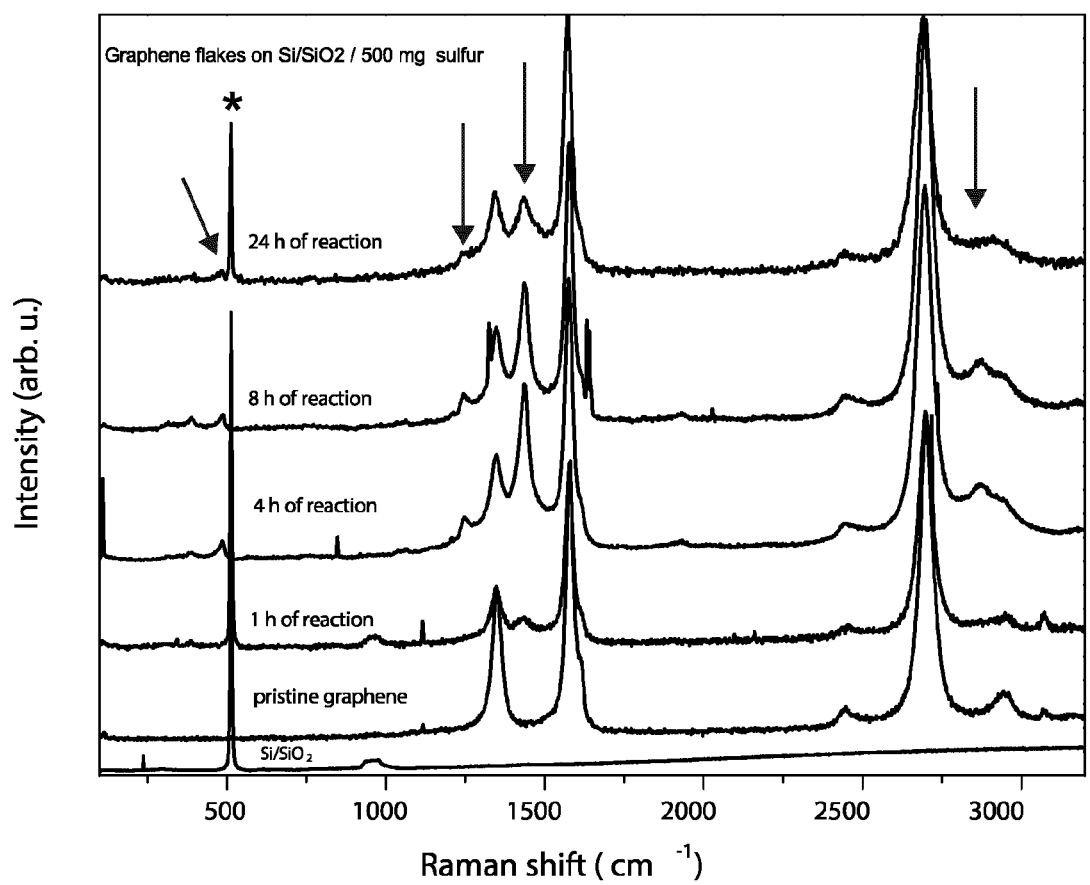
FIG. 2 displays typical (a) Raman spectra of sulfur-grafted graphene (top five lines) prepared according to Example 1 and pristine graphene (bottom line); (b) Raman spectra obtained before and after sulfur reaction at 470° C. on individualized SWCNTs and fullerenes (e.g. $C_{60}$) deposited on $Si/SiO_2$ as described in Example 1; and (c) X-ray photoelectron (XPS) spectra of sample RN884C obtained as in Example 1 after 8 h reaction with 500 mg of sulfur at 370° C.
Figure 2:
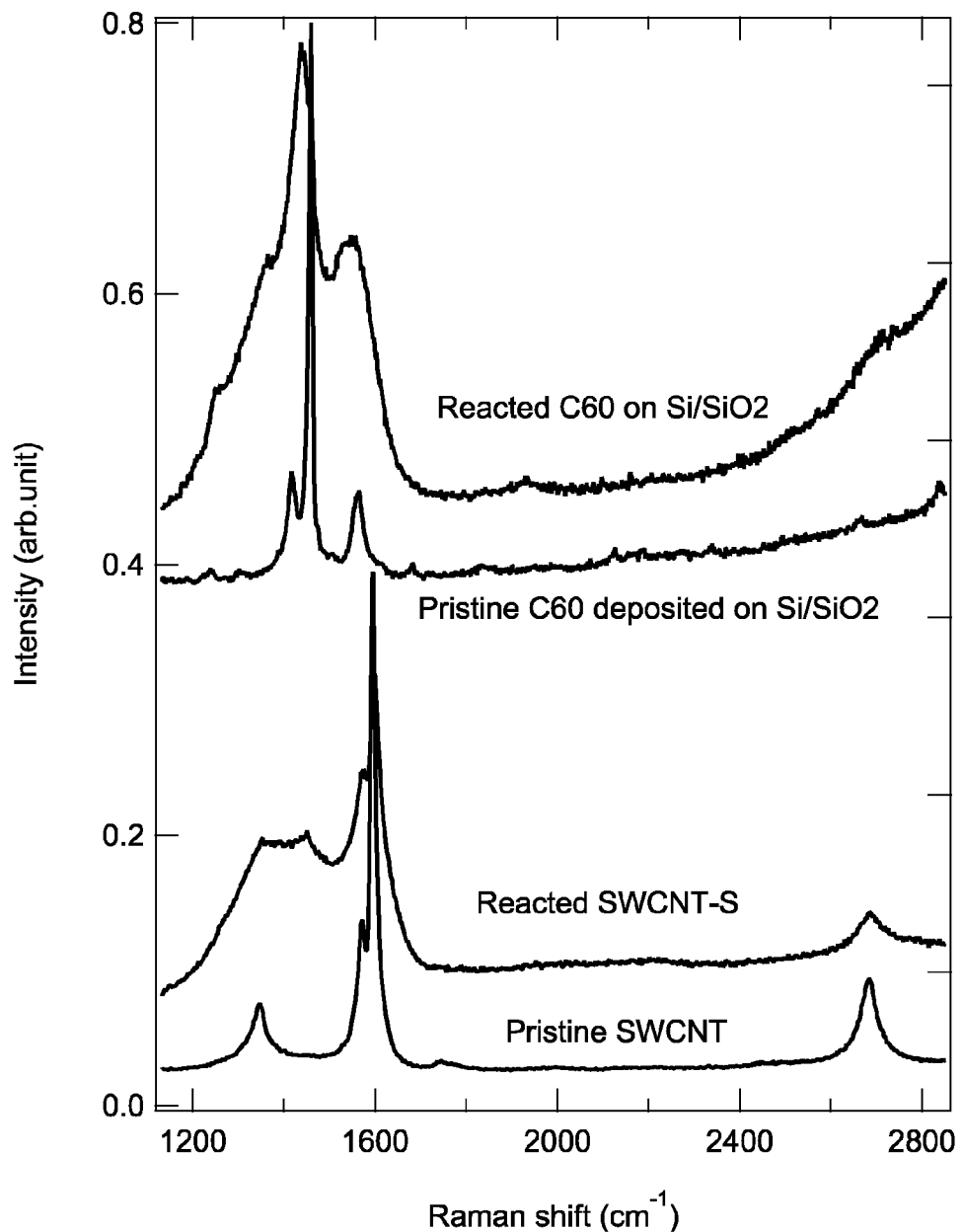
Figure 2:
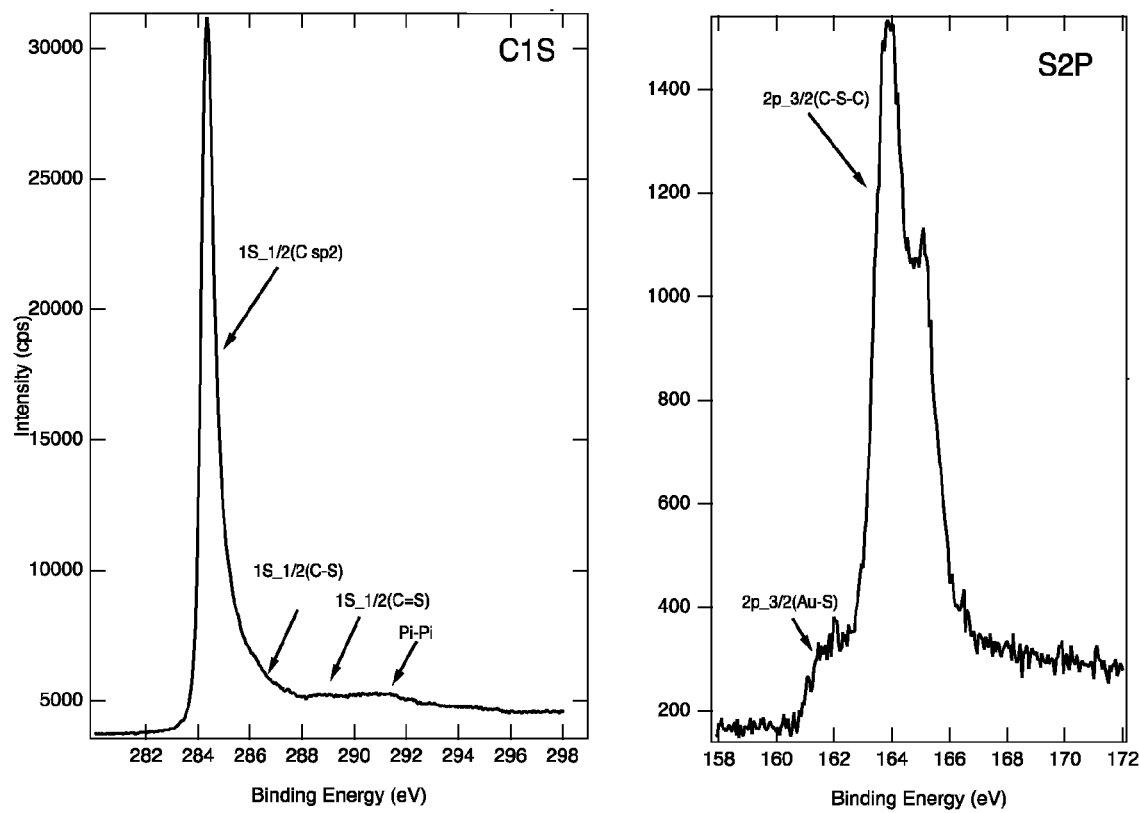

Raman spectra (FIG. 2(a)) of the graphene samples (RN869A, C, F, H) show a progression of the reaction and unambiguously demonstrate that the reaction is extensive after 24 hours. These are compared to a graphene-free Si/SiO$_2$ substrate obtained after heating the ampoule with sulfur at 450° C. (first curve from bottom, labelled Si/SiO$_2$), and to pristine graphene heated without sulfur at 450° C. (second curve from bottom, labelled pristine graphene). The * symbol indicates a substrate related mode. Not present in the starting graphene materials, broad peaks at 1435 cm$^{-1}$ and at 1240 cm$^{-1}$ have grown after 1 h, 4 h and 8 h reaction and these peaks are assigned to stretch $v(C(sp_2)SC(sp_2))$ and $v(—C(sp_2)=S)$, respectively. The evolution of these features (see black arrows) indicate direct bonding of the chalcogenide to the graphene surface, while the peaks at 1340 cm$^{-1}$, 1595 cm$^{-1}$, 2700 cm$^{-1}$, which are related to D, G and 2D bands of the starting graphene flakes (second curve), indicate the presence of unreacted graphene left after reaction. Residual unreacted sulfur (S$_8$) is also detected using the $v(S—S)$ mode at ~400 cm$^{-1}$ (see arrows). Similarly, the Raman spectra of the SWCNT sample (FIG. 2(b)) show the growth of the 1435 cm$^{-1}$ peak after 24 h reaction, which is also ascribed to the $v(C(sp_2)SC(sp_2))$ mode of the products. The presence of the peaks related to pristine SWCNTs located at 1330 cm$^{-1}$, 1590 cm$^{-1}$, 2700 cm$^{-1}$, i.e. the D, G and 2D bands, respectively, are slightly broadened and indicated the presence of unreacted SWCNTs. Reaction with other compounds such as carbon nanohorns and fullerenes (see FIG. 2b with C$_{60}$) also produce reaction products characterized with similar spectral features.

X-ray photoelectron spectra in FIG. 2(c) obtained after reaction of graphene flakes airbrushed on a gold-coated Si\SiO$_2$ substrate (RN884C, see Table 1 for reaction conditions) display a sulfur to carbon ration of 7% at the surface of the sample. The C1S region (left panel) indicates the presence of features at higher binding energy ascribed to C=S and C—S—C bonding. The S2P region (right panel) reveals a double peak related to the spin-orbit coupling with chemical shifts consistent with C—S—C bonding (i.e. sulfide S$^{-2}$ state) or unreacted S$_8$. It should be noted that elemental S$_8$ compounds display the same chemical shift in XPS. Residual contribution related to Au—S is also observed at low binding energy, which is due to a reaction between sulfure and gold substrate.

TEM mapping images in FIG. 3 of the obtained samples further confirm that the reaction is extensive and homogeneously distributed over the entire surface, as indicated by the distribution in EDS modes of C and S atoms co-localized at the surface of the produced material. The images also reveal that the backbone of the initial graphene samples is preserved after reaction. More specifically, FIGS. 3(a-d) present TEM images of grafted graphene, which clearly indicate that morphological integrity of the graphene flakes is preserved after reaction. The absence of free sulfur islands, clusters or nanoparticles is also noted from the TEM images.

FIGS. 3(e-v, x and z) present TEM images in Energy Dispersive X-ray Spectroscopy (EDS) mode. The rectangles in FIGS. 3(e, i, m, q, u) mark the region of the modified graphene that was investigated by EDS to produce TEM elemental mapping images. FIGS. 3(f, j, n, r, v) show the carbon distribution (in green) in the analyzed region, while FIGS. 3(g, k, o, s, x) show the sulfur distribution (in red). TEM mapping images resulting from colocalization of carbon and sulfur (obtained using COL Finder plugin of IMAGE J software), with C images as green channel and S images as red channel, indicate a significant correlation. For example, up to 99% of the pixels are correlated in FIGS. 3(h, l, p, t, z).

Figure 4:
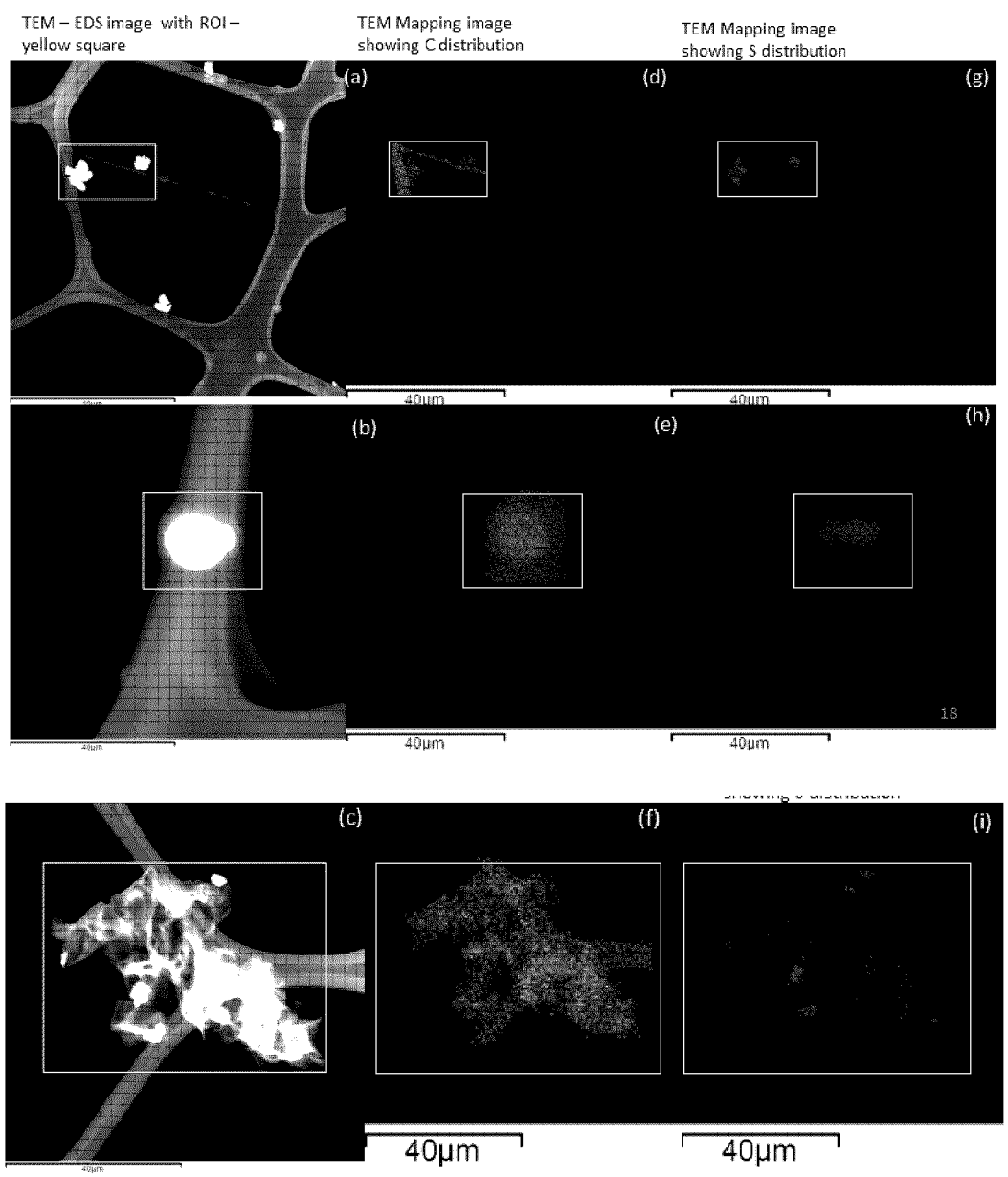
FIG. 4 shows (a)-(c) TEM images of a sample of mechanically mixed graphene and sulfur without reaction. The regions of interest (ROI) marked by squares are investigated further using EDS mode; (d)-(i) TEM-mapping images in EDS mode, where (d)-(f) show the carbon mapping distribution and (g)-(i) show the sulfur mapping distribution in TEM-mapping images in EDS modes, as detailed in Example 1.

FIG. 4 shows (a)-(c) TEM images of a sample obtained by mechanical mixing of graphene and sulfur. To show the difference relative to the sulfur-grafted graphene samples, this sample is investigated using EDS mode. FIGS. 4 (d)-(i) show EDS-mapping taken in the regions defined by squares, where (d)-(f) show the carbon mapping distribution in green of the samples on lacey carbon TEM grid and (g)-(i) show the sulfur mapping distribution in EDS modes. The images show that the sample has a heterogeneous distribution of sulfur on the graphene surface, showing islands of sulfur not related to the graphene and adsorbed on the lacey carbon TEM grid. This contrasts with the samples obtained by the procedure described here to prepare sulfur-grafted graphene and highlight the significant difference obtained with this method.

These results of the characterization of the products of the reaction indicate that this one-step, one-pot method provides access to an extensive reaction between graphene and chalcogenides. The method is free of chemical waste and provides high homogeneity in the carbon and chalcogenide (sulfur in this case) distributions (e.g. FIG. 3). Because it uses no solvent and generates no waste, the method is generally ecofriendly and very low cost compared to other methods and requires no pre- and post-treatment steps. That is, the unreacted chalcogen can readily be recovered and reused because of the temperature gradient in the oven.

Example 2: Test Results

(a) Electrochemical Properties

Self-supported electrodes were prepared using pure graphene and sulfur-grafted graphene (GS). The prepared electrodes were tested in lithium cells. FIG. 7 shows (a) graphene and (b) GS results of the preliminary galvanostatic cycling tests.

The graphene electrode showed no electrochemical activity under the testing conditions. Regarding the GS electrodes, three electrochemical processes were evidenced in discharge mode, i.e. a pseudo-plateau centered at 2.2V, a flat plateau at 2.0V and a sloppy decrease from 1.9 V (fast) to 1.3V. There are also two electrochemical processes evidenced in charge mode, i.e. a flat plateau at 2.25V and a sloppy increase between 2.3V to 2.6V.

(b) Coating of Aluminum Surfaces

Figure 8:
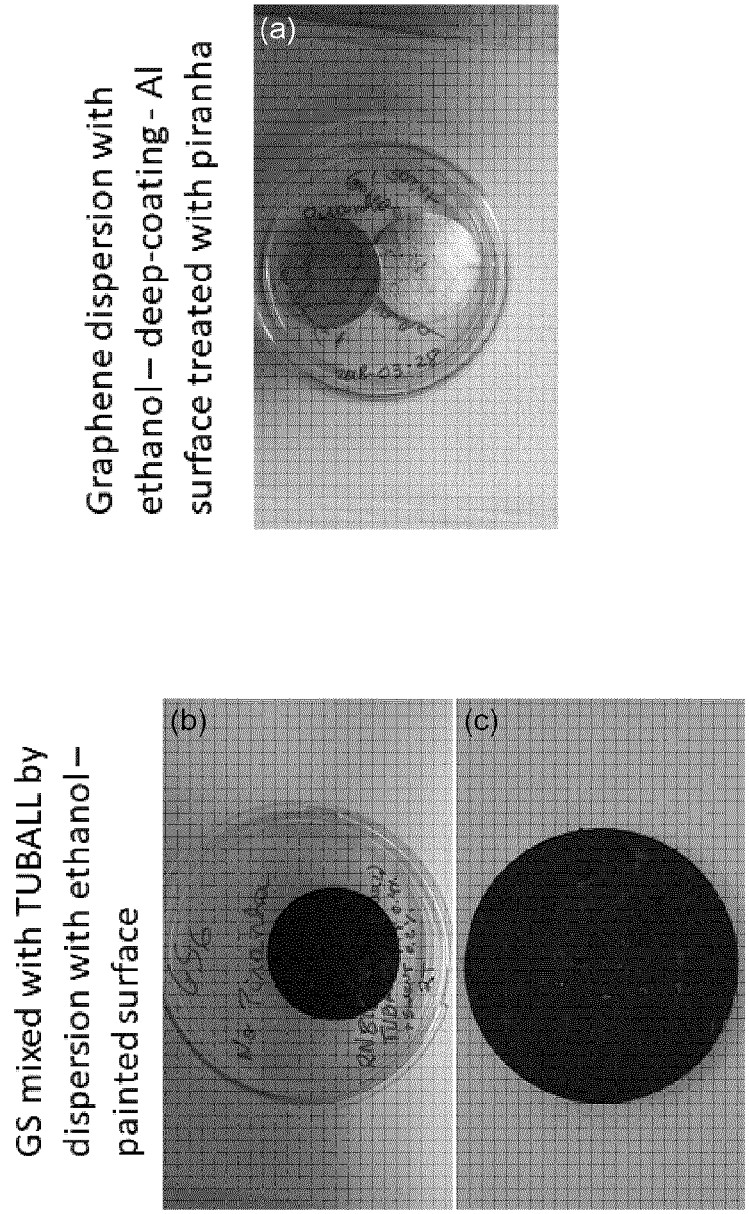
FIG. 8 shows (a)-(e) images of Al surfaces coated with (a) graphene; and (b)-(c) graphene-sulfur (GS) mixed with PVP+SWCNT (0.01%).

Aluminum surfaces were first treated with a piranha solution (sulfuric acid-hydrogen peroxide 3:1 vol:vol). The aluminum surfaces were dip-coated using a dispersion of graphene in ethanol or a dispersion of GS is ethanol; or were painted with a GS/ethanol dispersion mixed with PVP and SWCNTs (0.01%, Tuball™). FIGS. 8 (*a*)-(*e*) show images of Al surfaces coated with (a) graphene; (b)-(c) GS; and (d)-(e) GS mixed with PVP+SWCNT (0.01%). The presence of sulfur in GS resulted in improved adherence on the Al surface.

(c) Initial In Vitro Cytotoxicity

Graphene and the sulfur-grafted graphene (GS) were tested in a cell viability live/Dead™ assay. FIG. 9 shows the results obtained. The images show that the GS sample and graphene seem to have low impact on cell viability, allowing cell growth (cells in green) with very few dead cells (cells in red).

(d) Initial In Vitro Cytotoxicity

Figure 10:
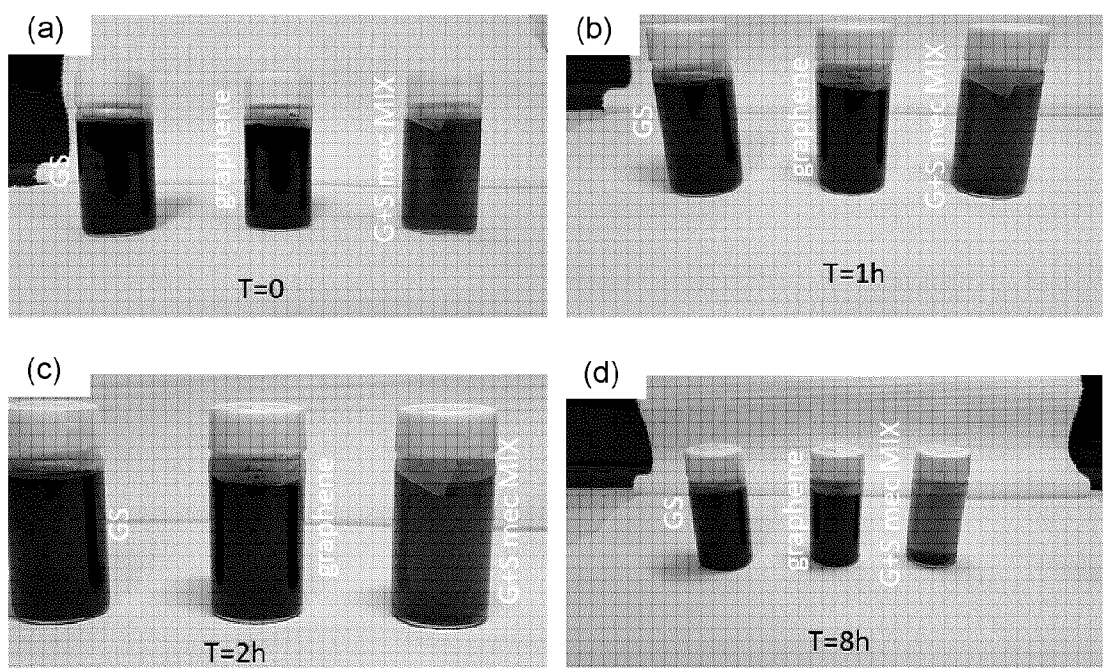
FIG. 10 presents images of a stability test of GS, graphene alone, and a graphene and sulfur mixed mechanically in ethanol, at times (a) 0 hour, (b) 1 hour, (c) 2 hours, and (d) 8 hours showing precipitation.

The sulfur-grafted graphene (GS) was further tested for stability as compared with graphene and a mechanical mixture of graphene and sulfur (G+S) using an equivalent quantity of each material in ethanol. FIG. 10 shows that a majority of G+S mixed sample has precipitated after 8 hours while the GS remains stable.

Numerous modifications could be made to any of the embodiments described above without deviating from the scope of the present invention. Any references, patents or scientific literature documents referred to in the present application are incorporated herein by reference in their entirety for all purposes.

The invention claimed is:

1. A chalcogen-grafted carbon material, wherein the chalcogen-grafted carbon material is a polyaromatic carbon material comprising a polyaromatic fused ring system, and the chalcogen X is covalently linked to the polyaromatic carbon material via C=X bonds on outside rings of said polyaromatic fused ring system and/or C—X—C bonds in the form of 3-membered rings on a surface of said polyaromatic fused ring system, wherein:

the chalcogen is a chalcogen other than oxygen,

C is a carbon atom from the polyaromatic fused ring system, and wherein the molar ratio of carbon:chalcogen in the chalcogen-grafted carbon material is within the range of from 2:1 to 1000:1.

2. The chalcogen-grafted carbon material of claim 1, wherein the molar ratio of carbon:chalcogen is within the range of from 3:1 to 100:1.

3. The chalcogen-grafted carbon material of claim 1, wherein the polyaromatic carbon material comprises 5-membered, 6-membered, 7-membered and optionally higher-membered rings in a fused rings system.

4. The chalcogen-grafted carbon material of claim 1, wherein the chalcogen-grafted carbon comprises units of at least one of the formulae:

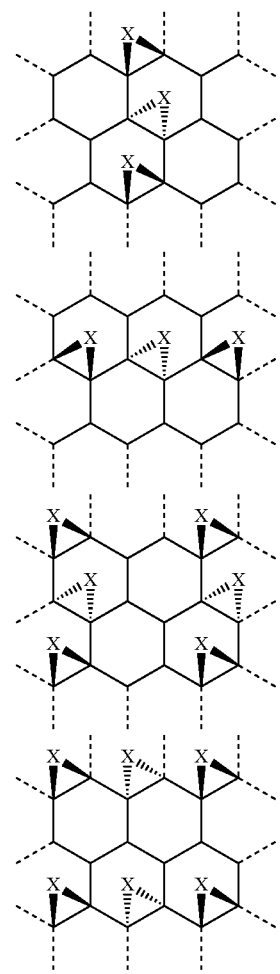

wherein X is selected from S, Se and Te.

5. The chalcogen-grafted carbon material of claim 4, wherein the chalcogen-grafted carbon further comprises C=X bonds.

6. The chalcogen-grafted carbon material of claim 1, wherein said polyaromatic carbon material is selected from graphene, graphite, carbon foams, and nanocarbons.

7. The chalcogen-grafted carbon material of claim 6, wherein said polyaromatic carbon material is graphene.

8. The chalcogen-grafted carbon material of claim 6, wherein said nanocarbons comprises nanohorns, fullerenes, and/or carbon nanotubes.

9. The chalcogen-grafted carbon material of claim 1, wherein X is selected from S, Se and Te.

10. The chalcogen-grafted carbon material of claim 9, wherein X is S.

11. The chalcogen-grafted carbon material of claim 10, wherein the concentration of chalcogen in the chalcogen-grafted carbon is from 1 wt % to 50 wt %.

12. The chalcogen-grafted carbon material of claim 11, wherein the concentration of chalcogen in the chalcogen-grafted carbon is from 3 wt % to 47 wt %.

13. A functionalized chalcogen-grafted carbon material, wherein the chalcogen-grafted carbon material is a polyaromatic carbon material comprising a polyaromatic fused ring system comprising C—X—C in the form of 3-membered rings on a surface of said polyaromatic fused ring system and C=X bonds on outside rings of said polyaromatic fused ring system, and is functionalized with —XH, —XR, or a combination thereof, or a complex or salt thereof, wherein X is a chalcogen covalently linked to the polyaromatic carbon material, and R is a functional group, or R is another X from the functionalized chalcogen-grafted carbon material thereby forming a C—X—X—C dichalcogenide bond, wherein the chalcogen is a chalcogen other than oxygen, and wherein C is a carbon atom from the polyaromatic carbon material.

14. The functionalized chalcogen-grafted carbon material of claim 13, wherein the polyaromatic carbon material is functionalized with —XH or a salt or a metal complex thereof.

15. The functionalized chalcogen-grafted carbon material of claim 13, wherein the C—X—C, C=X, —XH and/or —XR form a complex with a metal ion or a metal aggregate.

16. The functionalized chalcogen-grafted carbon material of claim 15, wherein the metal aggregate is selected from metallic nanoparticles made of a transition metal such as Pt, Ni, Co, Cu, Ru, Au and Ag.

17. The functionalized chalcogen-grafted carbon material of claim 16, wherein the transition metal is selected from Pt, Ni, Co, Cu, Ru, Au and Ag.

18. The functionalized chalcogen-grafted carbon material of claim 13, wherein the polyaromatic carbon material is functionalized with —XR, where R is an antibody tag, an alkyl, allyl, benzyl, phenyl, a polymer, MAL-PEG-NHS, SMCC-PEG-NHS, MAL-PEG-BIOTIN, SMCC-PEG-Biotin, or any other biocompatible polymers.

19. The functionalized chalcogen-grafted carbon material of claim 18, wherein the antibody tag is selected from SATA, SMCC, and SPDP.

20. A process for the preparation of a chalcogen-grafted carbon material, comprising the steps of:
(a) disposing a polyaromatic carbon material in a first compartment and a chalcogen in a second compartment, where the first and second compartments are connected to allow gaseous exchange without direct physical contact between the polyaromatic carbon and chalcogen; and
(b) simultaneously heating the first compartment at a first temperature and the second compartment at a second temperature;
wherein the first temperature is higher than the second temperature and wherein the second temperature allows the sublimation of the chalcogen;
wherein said chalcogen is a chalcogen other than oxygen.

21. The process of claim 20, wherein the first and second compartments are part of a dumbbell-shape ampoule.

22. The process of claim 20, wherein the first and second compartments are reactors.

23. The process of claim 20, wherein the first temperature is a temperature which is 500° C. or less, higher than the second temperature, or between 10° C. and 200° C. higher than the second temperature.

24. The process of claim 20, wherein the second temperature is within the range of from 100° C. to 950° C.

25. The process of claim 24, wherein the chalcogen X is Se and the second temperature is within the range of from 220° C. to 800° C., or from 180° C. to 650° C., or from 230° C. to 700° C., or from 200° C. to 600° C., or from 190° C. to 500° C.

26. The process of claim 24, wherein the chalcogen X is Te and the second temperature is within the range of from 350° C. to 950° C., or from 300° C. to 850° C., or from 550° C. to 750° C., or from 400° C. to 700° C., or from 550° C. to 950° C., or from 500° C. to 650° C., or from 330° C. to 550° C.

27. The process of claim 24, wherein the chalcogen X is S and the second temperature is within the range of from 100° C. to 650° C.

28. The process of claim 27, wherein the chalcogen X is S and the second temperature is within the range of from 150° C. to 650° C., or from 200° C. to 500° C., or from 150° C. to 450° C.

29. A process for producing a functionalized chalcogen-grafted carbon material, comprising the step of reacting a chalcogen-grafted carbon material as defined in claim 1 with a nucleophile, an oxidant, a reducing agent, a metal or a metallic salt or complex.

30. The process of claim 29, wherein the oxidant is $HNO_3$ or $O_2$ or wherein the reducing agent is $LiAlH_4$.

* * * * *